United States Patent [19]

Holzer

[11] Patent Number: 5,242,386
[45] Date of Patent: Sep. 7, 1993

[54] ECHOGRAPHIC SUCTION CANNULA

[75] Inventor: Eric Holzer, Stockton, Calif.

[73] Assignee: Sontech Limited, Dublin, Ireland

[21] Appl. No.: 937,346

[22] Filed: Aug. 27, 1992

[51] Int. Cl.$^5$ .............................................. A61B 17/20
[52] U.S. Cl. ........................................ 604/22; 604/19; 604/35; 604/902
[58] Field of Search .................. 604/19, 22, 27, 28, 604/35, 902; 606/169; 128/24 AA, 662.03, 662.06

[56] References Cited

U.S. PATENT DOCUMENTS

| | | | |
|---|---|---|---|
| 4,169,984 | 10/1979 | Parisi | 604/22 |
| 4,627,834 | 12/1986 | Lee | 604/902 |
| 4,815,462 | 3/1989 | Clark | 604/902 |
| 4,869,256 | 9/1989 | Kanno et al. | 128/662.06 |
| 4,886,491 | 12/1989 | Parisi et al. | 604/22 |
| 4,936,281 | 6/1990 | Stasz | 604/22 |
| 5,002,058 | 3/1991 | Martinelli | 128/662.06 |
| 5,058,570 | 10/1991 | Idemoto et al. | 128/24 AA |
| 5,069,664 | 12/1991 | Guess et al. | 128/662.06 |
| 5,123,903 | 6/1992 | Quaid et al. | 604/902 |
| 5,181,907 | 1/1993 | Becker | 604/902 |

FOREIGN PATENT DOCUMENTS 2559066  8/1985  France .............................. 604/902

Primary Examiner—Stephen C. Pellegrino
Assistant Examiner—Jeffrey A. Schmidt
Attorney, Agent, or Firm—Heller, Ehrman, White & McAuliffe

[57] ABSTRACT

An echographic suction cannula has an elongated suction tube with a closed front end and an open back end. Side openings are also provided for admitting therethrough material to be evacuated and discharged. An ultrasonic transducer is encased within the suction tube and partially exposed so as to be able to transmit and receive ultrasonic waves. An electrical cable extending longitudinally within the outer casing of the suction tube connects the transducer to an external circuit for controlling the operation of the transducer, causing pulse signals to be transmitted, receiving reflected signals and calculating the thickness of the layer of fatty tissues into which the front end of the cannula has been inserted.

12 Claims, 2 Drawing Sheets

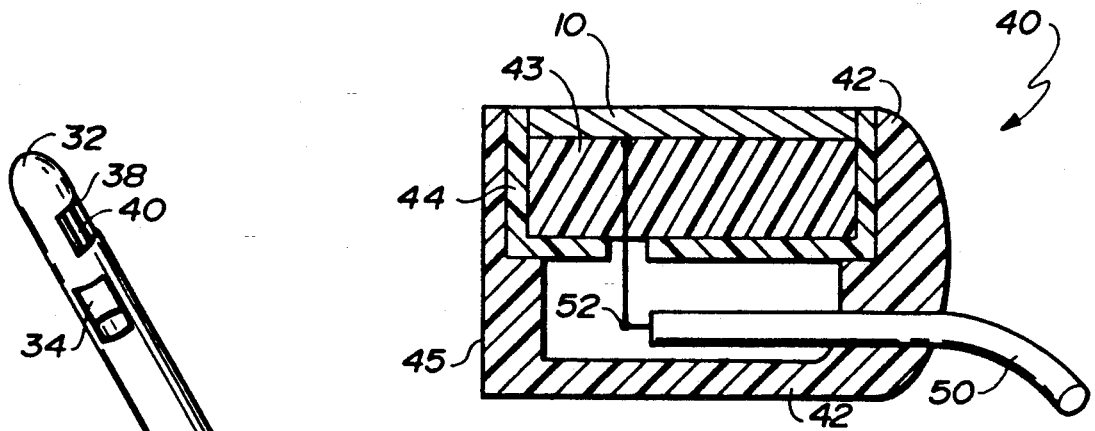
FIG._3
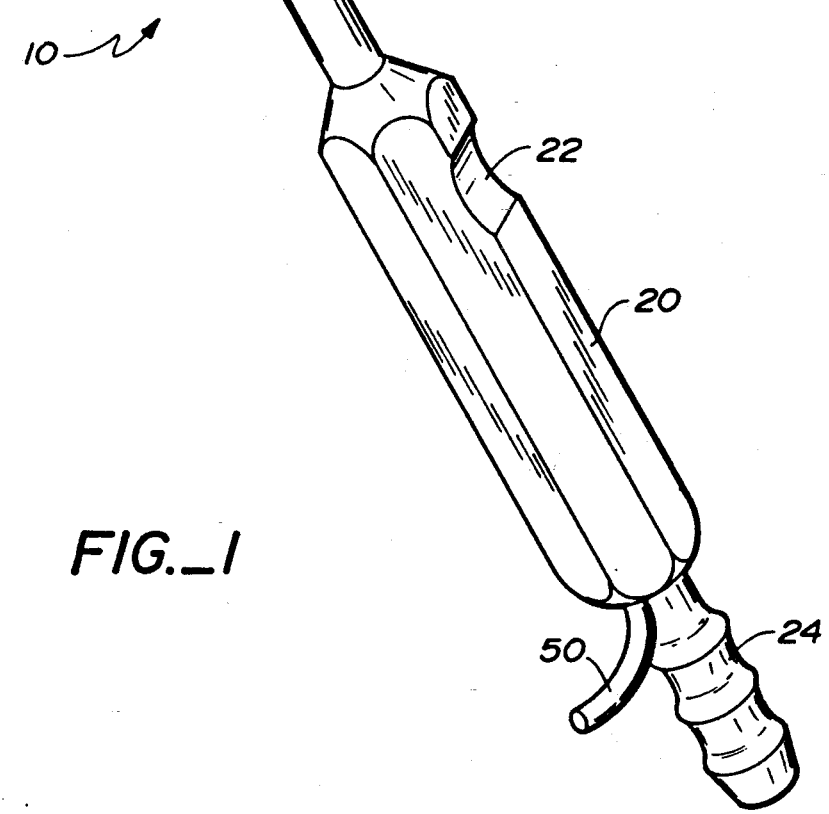
FIG._1

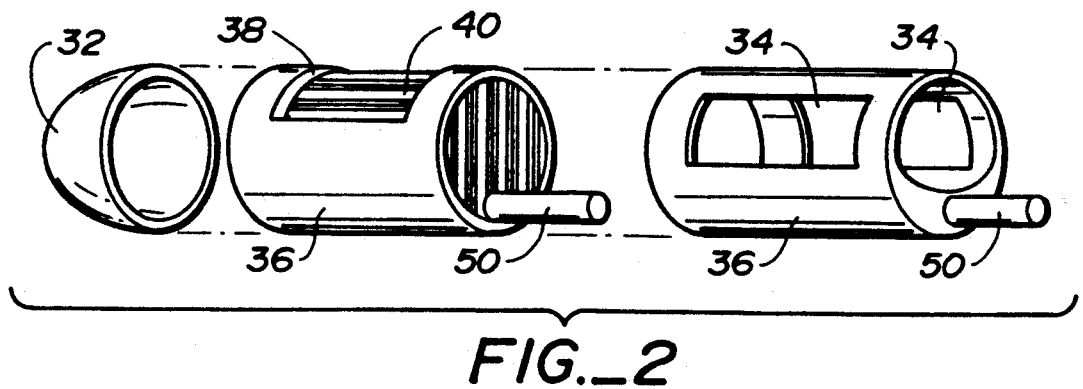
FIG._2
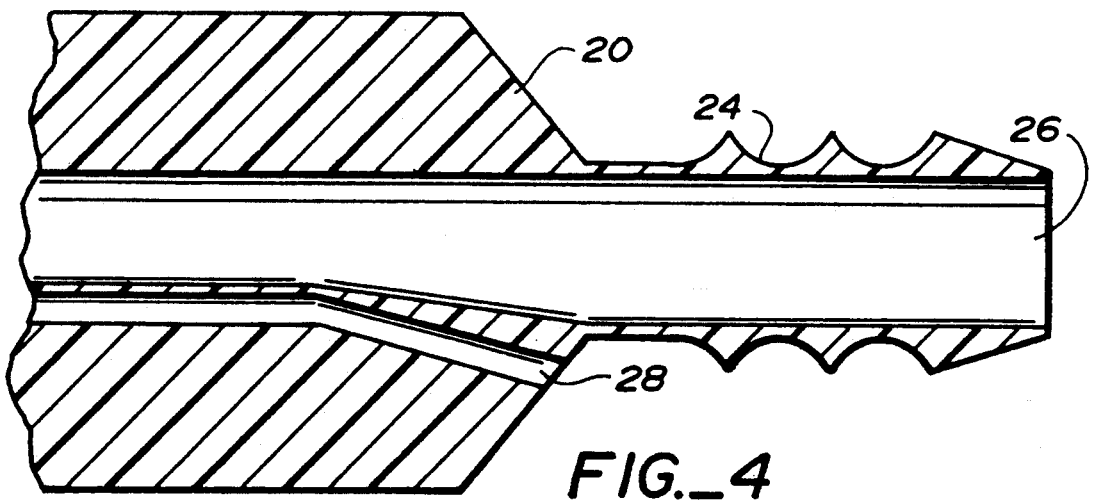
FIG._4

ECHOGRAPHIC SUCTION CANNULA

BACKGROUND OF THE INVENTION

This invention relates to an echographic suction cannula and, more specifically, to an improved medical device for liposuction.

Liposuction is a medical procedure for the aspiration and evacuation of fat from under the skin, and is performed by applying a negative pressure to a cannula, or a plain suction tube, which is moved under the skin surface through a small incision. With the devices currently available for liposuction, pinching of the skin is the only method of estimating the effect of liposuction during treatment on the thickness of fat remaining under the skin. Prior art suction cannulas for liposuction do not provide any means for precisely and continuously monitor the thickness of the remaining tissue during treatment, and the position of such cannulas within the tissue being treated can be estimated only by palpation. Consequently, surface irregularities and asymmetry were not uncommon, spoiling a large proportion of aesthetic results. This has also led to cannula malpositioning. A cannula, positioned too close to the dermis or to the muscle fascia, may cause surface dimples and furrows. If false passages are made into the deeper vital structure such as intra-abdominal organs, the consequence of cannula malpositioning can be serious enough to be life-threatening.

Tissue thickness can be measured and displayed by current medical imaging techniques, such as ultrasonography, xeroradiography or magnetic resonance imaging, but their use during liposuction would require interruptions of the operation, and contaminated heavy equipment would have to be brought to the sterile field. Moreover, the equipment would have to be retrieved before the operation can be resumed, and this would have to be repeated any number of times during an operation. As a result, such currently available imaging techniques are seldom used during liposuction and are primarily reserved for pre-operative and post-operative evaluations.

It is therefore a general object of the present invention in view of the above to provide a suction cannula which can make liposuction a safer procedure and to thereby make it possible to obtain a larger proportion of pleasant aesthetic results.

It is a more specific object of the present invention to provide a suction cannula for liposuction which will, when connected to an appropriate electronic circuitry, allow continuous, precise monitoring, visual display and recording of the thickness of fatty tissue.

It is another object of the present invention to provide such a suction cannula which also allows display and recording of the position of the cannula within the thickness of the tissue being treated.

SUMMARY OF THE INVENTION

A suction cannula, with which the above and other objects can be accomplished, may be characterized as having a handle and a suction tube longitudinally extending therefrom and containing near its tip an ultrasonic transducer. The transducer is partially exposed through a side window so as to be able not only to transmit ultrasonic pulse signals therethrough but also to receive their echoes. The suction tube is provided with suction openings through which fatty tissues are introduced into the tube to be evacuated, the window for the transducer being situated between the tip and these suction openings. A coaxial cable which connects the transducer to an external circuit passes substantially parallel to a central passage for the fatty tissues to be evacuated but within the outer casing of the suction tube so as not to obstruct the flow inside the central passage. The handle has a thumb grip indicative of the angular position of the transducer window with respect to the longitudinal axis of the suction pipe. The position of the cannula within the tissue being treated can be determined by analyzing the time delay between the electric pulse delivered to the transducer and that from the transducer in response to a received echo. The user can have this information displayed as a simultaneous and continuous image during a liposuction treatment.

BRIEF DESCRIPTION OF THE DRAWINGS

The accompanying drawings, which are incorporated in and form a part of this specification, illustrate an embodiment of the invention and, together with the description, serve to explain the principles of the invention. In the drawings:

FIG. 1 is a perspective view of an echographic suction cannula embodying the present invention;

FIG. 2 is an exploded view of the tip part of the cannula of FIG. 1;

FIG. 3 is a sectional side view of the ultrasonic transducer within the tip part of FIG. 2; and FIG. 4 is a side sectional view of the handle part of the cannula of FIG. 1.

DETAILED DESCRIPTION OF THE INVENTION

With reference to FIG. 1, an echographic suction cannula 10 according to the present invention may be made of a stainless steel, plastic or carbon material, and consists essentially of a handle 20 at its proximal (to the user's hand) end and a hollow suction tube 30 extending forward from the handle 20. The suction tube 30 has a bluntly rounded tip 32 at its forward end distal from the handle 20, its outer casing 36 having one or more suction openings 34 (only one such opening being visible in FIG. 1) on its side surface near the cannula tip 32. An ultrasonic transducer assembly 40 is contained within the suction tube 30 between the cannula tip 32 and the suction opening 34, partially exposed through a window 38 in the casing 36 such that a 3° signal aperture is provided. The assembly 40 is connected to an external electric pulse generating and processing circuit (not shown) through a coaxial cable 50 which runs longitudinally through the outer casing 36 of the suction tube 30, as more clearly shown in FIG. 2, and exits at the base of the handle 20, as shown in FIG. 1. The handle 20 is provided with a thumb grip 22 at the same angular location as the window 38 for the transducer assembly 40 around the longitudinal axis of the suction tube 30. The handle 20 is also provided at its back with a tubing grip 24 around the backward extension of the suction tube 30 for making connection to a tubing attached to an vacuum chamber (not shown) serving as a source of negative pressure.

With reference next to FIG. 2, which shows more in detail the arrangement of the ultrasonic transducer assembly 40 within the suction tube 30, the ultrasonic transducer assembly 40 is situated very close to the suction openings 34. As shown in FIG. 3, the transducer assembly 40 includes a piezoelectric element 41 connected to a live wire 52 within the coaxial cable 50. Ground terminals 42 are provided both on the outer surface of the piezoelectric element 41 and within the transducer assembly 40, both connected to the coaxial cable 50. The piezoelectric element 41 is supported by a vibration-buffering backing block 43, which is itself surrounded by an acoustic insulator 44 and a plastic case 45.

With reference next to FIG. 4, there is a central passage 26 through the suction tube 30 and the handle 20 for transporting separated fatty tissues from the suction openings 34 backward towards the back end of the handle 14. A narrower longitudinal passage 28, containing the coaxial cable 50 therein runs substantially parallel to the central passage 26, moving away therefrom as shown in FIG. 6 near the backward end of the handle 20.

When use is made of an echographic suction cannula 10 thus structured, an incision is made and the cannula tip 32 is guided through the skin into the layer of fatty tissues below. Since the tip 32 is rounded and blunt, the cannula 10 can be inserted in a non-traumatic manner. With a negative pressure applied through the central passage 26, fat is aspirated through the suction openings 34 into the central passage 26 and evacuated outside when tubing (not shown) is secured over the tubing grip 24 and connected to an external vacuum chamber (not shown) as explained above. The relative positions of the suction openings 34 and the tip 32, as well as the path of the coaxial cable 50 within the outer casing 36, provide unobstructed evacuation of the fat.

Sonar depth measurement by the echographic suction cannula 10 as described above is achieved according to the present invention by connecting the external end of the coaxial cable 50 to an external circuit (not shown) for generating and processing electric pulse signals. A first electric pulse of very short duration (say, no more than 100 nanoseconds) is delivered to the piezoelectric element 41, thereby causing a short bout of ultrasonic vibrations to be produced and propagated to the fatty tissue through the transducer window 38 providing 3° signal aperture. These ultrasonic waves travel through fatty tissues with the speed of 1460 m/sec and are reflected at the interface between echolucent fat and echogenic dermis and muscle fascia, returning and stimulating the exposed piezoelectric element 41. Thereupon, the piezoelectric element 41 produces an electric pulse signal, which is received through the coaxial cable 50, filtered and amplified by the external pulse-processing circuit.

The time lapse between the initial delivery of the pulse to the piezoelectric element 41 and the receipt of echo thereby is indicative of the tissue thickness at the position of the transducer, and this information can be displayed on a computer video screen or the like in a known manner. Since fatty tissues susceptible to liposuction treatment almost never exceeds 0.5 meters, the elapsed time almost never exceeds 1 millisecond. This means that such pulses can be delivered to the piezoelectric element 41 at a sufficiently high rate so as to provide a seemingly continuous sequence of image without the fear of interference between pulses.

With reference back to FIG. 3, the backing block 43 surrounded by the acoustic insulator 44 serves to prevent the vibrations of the piezoelectric elements 41 from causing the so-called ringing phenomenon The thumb grip 22 is on the handle 20 so as to point in the same direction as the propagation of the ultrasonic waves.

Thus, by rotating the cannula 10 around its longitudinal axis, the ultrasonic waves can be directed selectably towards the superficial plane, dermis or muscle fascia by using the thumb grip 22 as visual pointer. As a practical procedure, the user may first position the tip 32 just above the muscle fascia under visual control by using the video screen, with the thumb grip 22 directed towards the depth to keep monitoring the distance to the muscle fascia. Next, the thumb grip 22 is rotated towards the surface and liposuction is carried out in that plane while the total thickness of the fatty tissues is being displayed with the cannula 10 remaining in the same position.

The invention has been described above by way of only one typical example, but this example is intended to be illustrative, not as limiting the scope of the invention. In fact, many modifications and variations are possible within the scope of the invention. For example, both the number and the shape of the suction openings 34 may be varied. The thumb grip 22 is not an indispensable component on the handle 20. It can be replaced by another surface marking or means for pointing the direction of the transducer window 38. The dimensions of the cannula 10 itself can be varied. Availability of cannulas 10 with different diameters and lengths is definitely advantageous. Smaller ones, say, with a diameter of 1.5 mm, will need a smaller ultrasonic transducer with higher frequencies up to 20 Mhz and hence shorter wave penetration, and may be suited for working just below the level of the surface of the skin. Larger ones, say, with cannula diameter of up to 10 mm or more, may have larger transducers of low frequencies of 4 Mhz or less with deeper tissue penetration and are suited for work in the depth of a thick fatty tissue layer. The piezoelectric element 41 may be provided with an acoustic lens for focusing, or may be left unfocused as in the case of the example illustrated wherein.

The external electric circuit, to which the cannula 10 of the present invention is to be connected, may be for purposes other than the thickness display Connection may be made, for example, to a circuit for automatic control of suction pressure or for regulating suction flow by opening and closing an external valve (not shown). The cannula 10 of the present invention may also be made compatible with currently available ultrasonographic equipment present at most hospitals.

It is also to be noted that this invention, with or without the handle 20, can be used on any fluid or body susceptible to be evacuated by suction, with the advantage of capability to monitor and measure fluid level and automatically regulate the suction flow according to the thus monitored or measured level. Thus, the number of ultrasonic transducers and coaxial cables within the cannula 10 may vary so as to enable continuous and simultaneous monitoring and measurements of distances in different directions. In summary, all such modifications and variations that may be apparent to a person skilled in the art are intended to be included within the scope of the invention.

What is claimed is:
1. An echographic suction cannula comprising:
an elongated suction tube comprised of an outer casing having a closed front end and an open back end, said suction tube also having side openings, near the front end, for admitting therethrough material to be evacuated through said open back end;

an ultrasonic transducer encased within said suction tube between said front end and said side openings and partially exposed externally, said transducer being capable of transmitting and receiving ultrasonic waves;

an electrical cable electrically connected to said transducer, said cable extending longitudinally within said outer casing between said transducer and an outlet near said back end of said suction tube.

2. The device of claim 1 wherein said suction tube is further provided with a side window through which said transducer is partially exposed and through which said transducer is capable of transmitting and receiving ultrasonic waves.

3. The device of claim 2 further comprising a handle around said suction tube near said back end, said handle having thereon means for indicating the angular orientation of said side window.

4. The device of claim 1 wherein said transducer is capable of transmitting ultrasonic waves of 4–20 MHz.

5. The device of claim 1 further comprising an acoustic insulator surrounding backing means for preventing vibrations of said transducer from causing ringing phenomenon.

6. The device of claim 1 further comprising means close to said back end of said suction tube for gripping a vacuum tubing for connecting said suction tube to a source of negative pressure.

7. A method of evacuating materials by suction, said method comprising the steps of:

selecting an echographic suction cannula having an elongated suction tube with a closed front end, an open back end and suction openings, near the front end, said suction tube encasing therein an ultrasonic transducer between said front end and said suction openings, said ultrasonic transducer being partially exposed through a side window near said closed front end of said suction tube;

inserting said front end of said cannula into a target position in a layer of tissue having thickness;

causing said transducer to transmit ultrasonic waves and to receive reflected waves to thereby measure said thickness of said layer of tissue; and applying suction to thereby evacuate materials from said layer of tissue through said suction openings.

8. The method of claim 7 wherein said target position is under the skin of a body and said materials comprise fatty tissues.

9. The method of claim 8 further comprising the step of initially inserting said suction tube into said target position close to muscle fascia through an opening in the skin with said transducer transmitting ultrasonic waves towards the muscle fascia.

10. The method of claim 8 further comprising the step of subsequently rotating said suction tube such that said transducer transmits waves towards said opening in the skin.

11. The method of claim 7 wherein said ultrasonic waves caused to be transmitted from said transducer are in the range of 4–20 MHz.

12. The method of claim 7 wherein said transducer is caused to transmit said ultrasonic waves by delivering a transducer-energizing electric pulse signal to said transducer.

* * * * *